US006785360B1

(12) United States Patent
Annis (10) Patent No.: US 6,785,360 B1
(45) Date of Patent: Aug. 31, 2004

(54) PERSONNEL INSPECTION SYSTEM WITH X-RAY LINE SOURCE

(76) Inventor: Martin Annis, 65 Banks St., Cambridge, MA (US) 02138

( * ) Notice: Subject to any disclaimer, the term of this patent is extended or adjusted under 35 U.S.C. 154(b) by 0 days.

(21) Appl. No.: 10/288,244

(22) Filed: Nov. 5, 2002

Related U.S. Application Data (63) Continuation-in-part of application No. 09/897,715, filed on Jul. 2, 2001, now Pat. No. 6,628,745.
(60) Provisional application No. 60/337,299, filed on Nov. 5, 2001.

(51) Int. Cl.[7] .............................................. H01J 35/30
(52) U.S. Cl. ........................ 378/137; 378/90; 378/143; 378/57
(58) Field of Search ......................... 378/90, 137, 143, 378/57

(56) References Cited

U.S. PATENT DOCUMENTS

| | | | |
|---|---|---|---|
| 3,780,291 A | | 12/1973 | Stein et al. |
| 4,281,251 A | | 7/1981 | Thompson et al. |
| 4,298,800 A | * | 11/1981 | Goldman ..................... 378/19 |
| 4,521,900 A | | 6/1985 | Rand |
| 5,119,408 A | * | 6/1992 | Little et al. ..................... 378/4 |
| 5,260,982 A | * | 11/1993 | Fujii et al. ..................... 378/87 |
| 6,009,146 A | * | 12/1999 | Adler et al. ............... 378/98.6 |
| 6,104,776 A | * | 8/2000 | Oikawa ....................... 378/22 |
| 6,421,420 B1 | * | 7/2002 | Grodzins ................... 378/98.6 |
| 6,442,233 B1 | * | 8/2002 | Grodzins et al. ............. 378/57 |

* cited by examiner

Primary Examiner—Craig E Church
Assistant Examiner—Jurie Yun
(74) Attorney, Agent, or Firm—Inna Shtivelband Landsman; Dennis F. Armijo (57) ABSTRACT

A personnel x-ray inspection system includes an electron source that provides a pencil beam of electrons. An electromagnet assembly receives the pencil beam of electrons and directs the beam of electrons along a line to form a scanning redirected beam under the control of a scan command signal. The scanning redirected beam strikes a target and generates a cone of x-rays that moves along a target line as a result of the scanning redirected beam. A collimator receives the scanning cone of x-rays and generates a collimated traveling pencil beam, which is directed to a person under inspection. A moving platform translates the person under inspection through the collimated traveling pencil beam. A backscatter detector detects backscattered x-rays, and provides a backscattered detected signal indicative thereof. A system controller provides the scan command signal, and also receives and processes the backscattered detected signal.

12 Claims, 10 Drawing Sheets

PERSONNEL INSPECTION SYSTEM WITH X-RAY LINE SOURCE

PRIORITY DATA

This application claims priority from provisional application designated Serial No. 60/337,299 filed Nov. 5, 2001 and entitled "Personnel Inspection System with X-Ray Line Source", and is a continuation-in-part of utility patent application Ser. No. 09/897,715 entitled "Imaging With Digital Tomography and a Rapidly Moving X-ray Source", filed Jul. 2, 2001, now U.S. Pat. No. 6,628,745. Both applications are hereby incorporated by reference.

BACKGROUND OF THE INVENTION

The present invention relates to the field of x-ray inspection systems, and in particular to an x-ray inspection for inspecting personnel.

The x-ray systems currently used to inspect people are based on using a scanning pencil beam of x-rays to produce an x-ray backscatter image. The pencil beam is formed by two collimators. The first collimator is a fixed slit and the second collimator is a rotating slit. As the rotating slit passes across the fixed slit, a single line of data is formed. For example, see U.S. Pat. No. 3,780,291 entitled "Radiant Energy Imaging With Scanning Pencil Beam" by Stein et al. Subsequent lines of data are produced by translating the entire pencil beam forming apparatus across the body of the person under inspection. These systems typically operate at 70–140 KV peak.

A problem with these systems is that they are rather large, and require an x-ray source that includes a rotating collimator.

Therefore, there is a need for an improved personnel x-ray inspection, including a personnel x-ray inspection system that includes an x-ray source which provides a collimated traveling pencil beam of x-rays without the need for a moving (e.g., rotating) collimator assembly.

SUMMARY OF THE INVENTION

Briefly, according to an aspect of the present invention, a personnel x-ray inspection system includes an electron source that provides a pencil beam of electrons. An electromagnet assembly receives the pencil beam of electrons and directs the beam of electrons along a straight line under the control of a scan command signal to form a scanning redirected beam. The scanning redirected beam strikes a target and generates a cone of x-rays that moves along a straight target line as a result of the scanning redirected beam. A collimator receives the scanning cone of x-rays and generates a collimated traveling pencil beam, which is directed to a person under inspection. A moving platform translates the person under inspection relative to the collimated traveling pencil beam. A backscatter detector detects backscattered x-rays, and provides a backscattered detected signal indicative thereof. A system controller provides the scan command signal, and also receives and processes the backscattered detected signal to provide an image signal indicative of the person under inspection.

In a first embodiment, the personnel x-ray inspection system includes a rotating base on which the person under inspection stands to rotate the person under inspection relative to the collimated traveling pencil beam of x-rays. In a second embodiment, the system includes a moving platform on which the person under inspection stands to translate the person under inspection longitudinally relative to the collimated traveling pencil beam of x-rays. In this second embodiment, the person is then turned around and translated again through the collimated traveling pencil beam of x-rays.

Advantageously, the personnel x-ray inspection system uses a scanning pencil beam, and produces a line of data without requiring any moving parts. In addition, subsequent lines of data are produced without moving the collimator.

The pencil beam preferably moves repetitively in a straight line that does not translate as the image is formed. The translation is produced by the motion of the person being inspected. This feature allows the use of a relatively narrow beam catcher for the x-rays. The beam catcher is mounted behind the person and may be a few inches wide by about six feet long.

These and other objects, features and advantages of the present invention will become more apparent in light of the following detailed description of preferred embodiments thereof, as illustrated in the accompanying drawings.

DETAILED DESCRIPTION OF THE INVENTION

Figure 1:
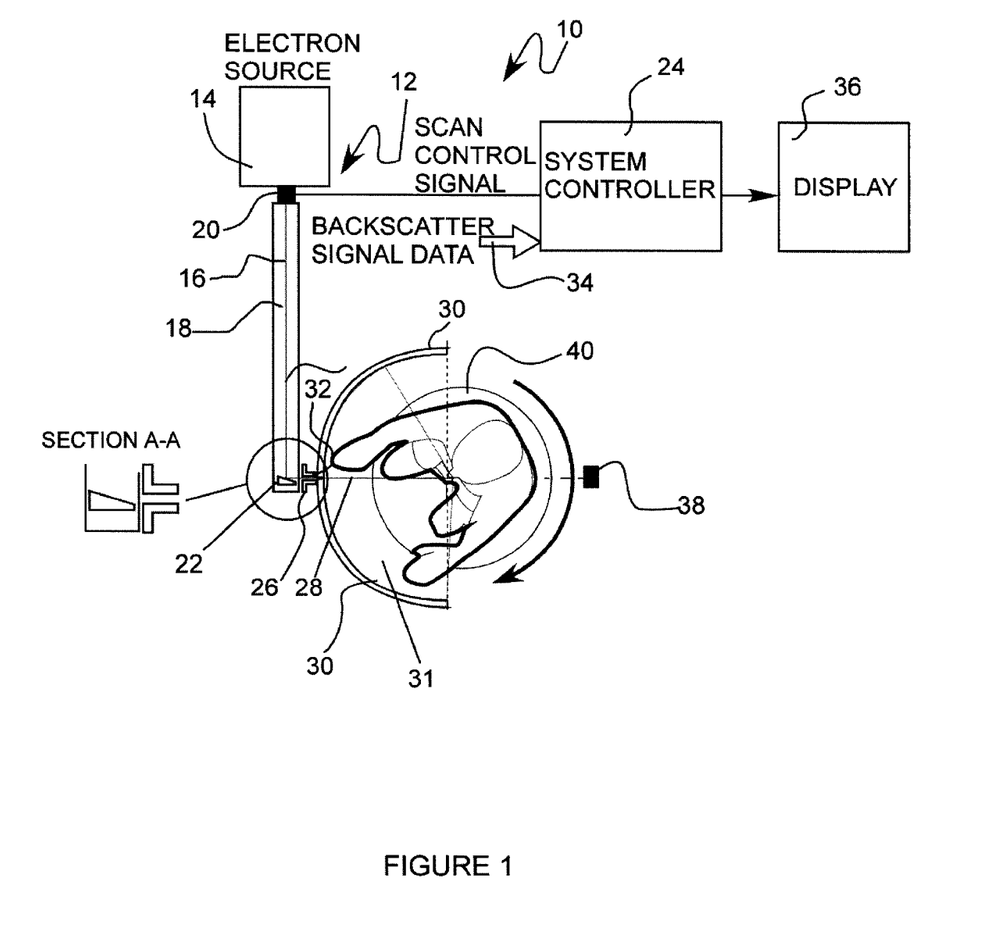
FIG. 1 is a top view of a personnel x-ray inspection system.

FIG. 1 illustrates a top view of a personnel x-ray inspection 10. The system includes an x-ray source 12, which includes an electron accelerator 14 that provides a monoenergetic electron beam 16, for example in the range of about 70 to 200 KeV (preferably 70–150 KeV), which enters a vacuum chamber 18 that includes an electromagnet assembly 20. The electron beam 16 is deflected across an x-ray anode 22 (e.g., tungsten, gold, et cetera), preferably by an electric field established by the electromagnet assembly 20 operating under the control of a system controller 24. As the deflected electron beam 16 strikes the target 22 along a straight line, a cone of x-rays is formed that travels rapidly along a straight line. The cone of x-rays is input to slit collimator 26, which provides a collimated traveling pencil beam of x-rays 28.

Figure 2:
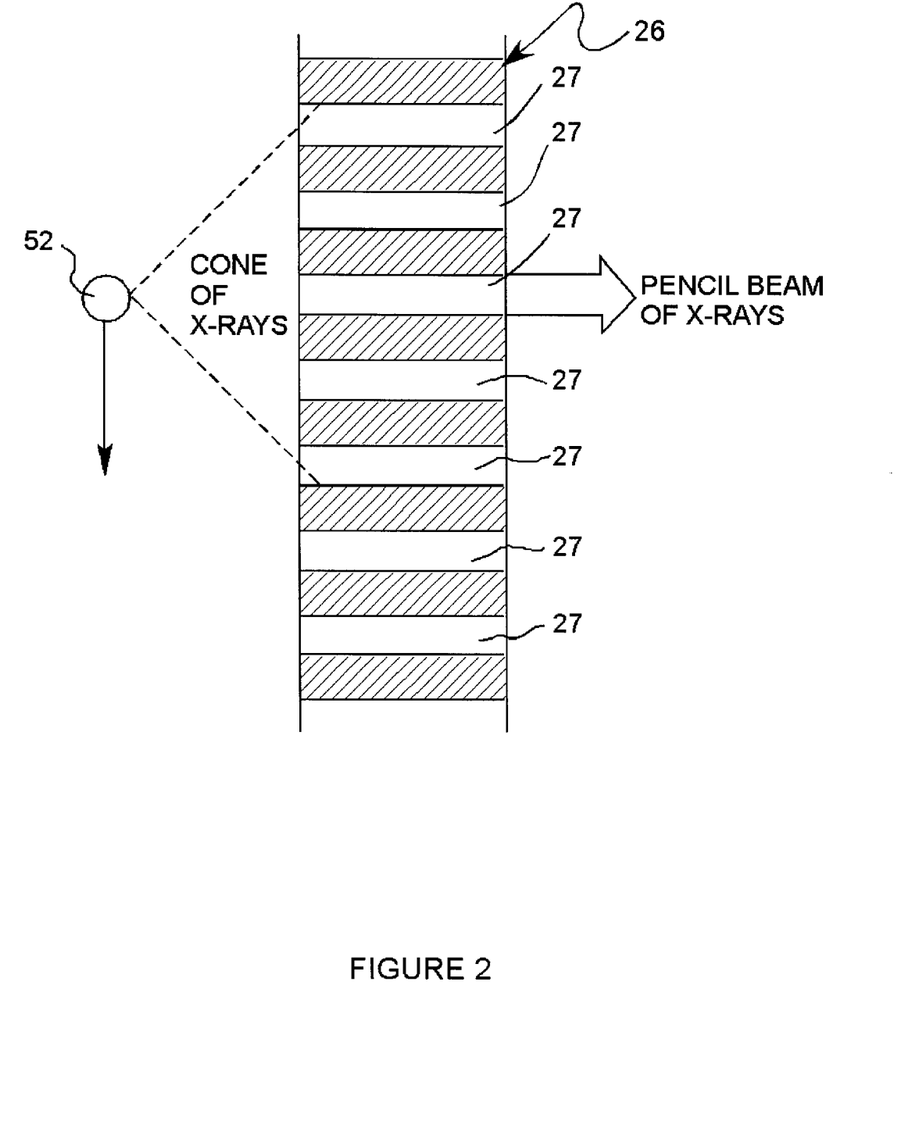
FIG. 2 is a cross sectional illustration of the collimator.

FIG. 2 is a cross sectional illustration of the collimator 26. The collimator includes a row of small holes 27 in a bar (e.g., tungsten, iron or lead) thick enough to absorb the x-ray beam in the area between the holes 27. In addition, the holes must be deep enough so that the x-rays that are not normal to the collimator 26 do not pass through the adjacent holes (i.e., only one hole in the collimator allows x-rays to pass through the collimator at any time). These holes/slots may be about one (1) mm square.

Referring again to FIG. 1, the system 10 also includes an x-ray backscatter detector 30, arranged adjacent to the collimator 26. The x-ray backscatter detector 30 preferably includes a scintillating material (e.g., plastic scintillating material) and plurality of x-ray detector elements, such as for example photomultipliers, photodiodes, et cetera. The traveling pencil beam 28 strikes the person under inspection, and backscattered x-rays 31 are detected by the backscatter detectors. As shown, in one embodiment, the backscatter detector 30 is arranged in a semi-cylindrical shape, and a vertical slit 32 bisects the backscatter detector to allow the collimated traveling pencil beam 28 to pass. The backscatter detector 30 provides electrical signals 34 indicative of the detected backscattered x-rays to the system controller 24, which forms an image. The image may be presented on a display 36 to a system operator. The system 10 also includes a beam catcher 38 positioned to capture x-rays that pass through the person under inspection.

The system produces a line of image data along the entire height of the person being inspected. Subsequent lines of data are produced by rotating the body of the person, who is standing on a rotating base 40, and rescanning the electron beam along the target line to form the vertically traveling pencil beam. The time for a single line of data is approximately 5 milliseconds, so 1000 lines will be produced in 5 seconds. Approximately 500 slots are sampled twice each to form 1000 independent pixels (Nyquist Theorem). The backscatter x-ray image is preferably a "development" of the surface of the human body. Thus, the image is preferably not a picture of the subject, but rather a detailed "map" of the surface of the body. The image is therefore not an invasion of privacy.

Figure 3:
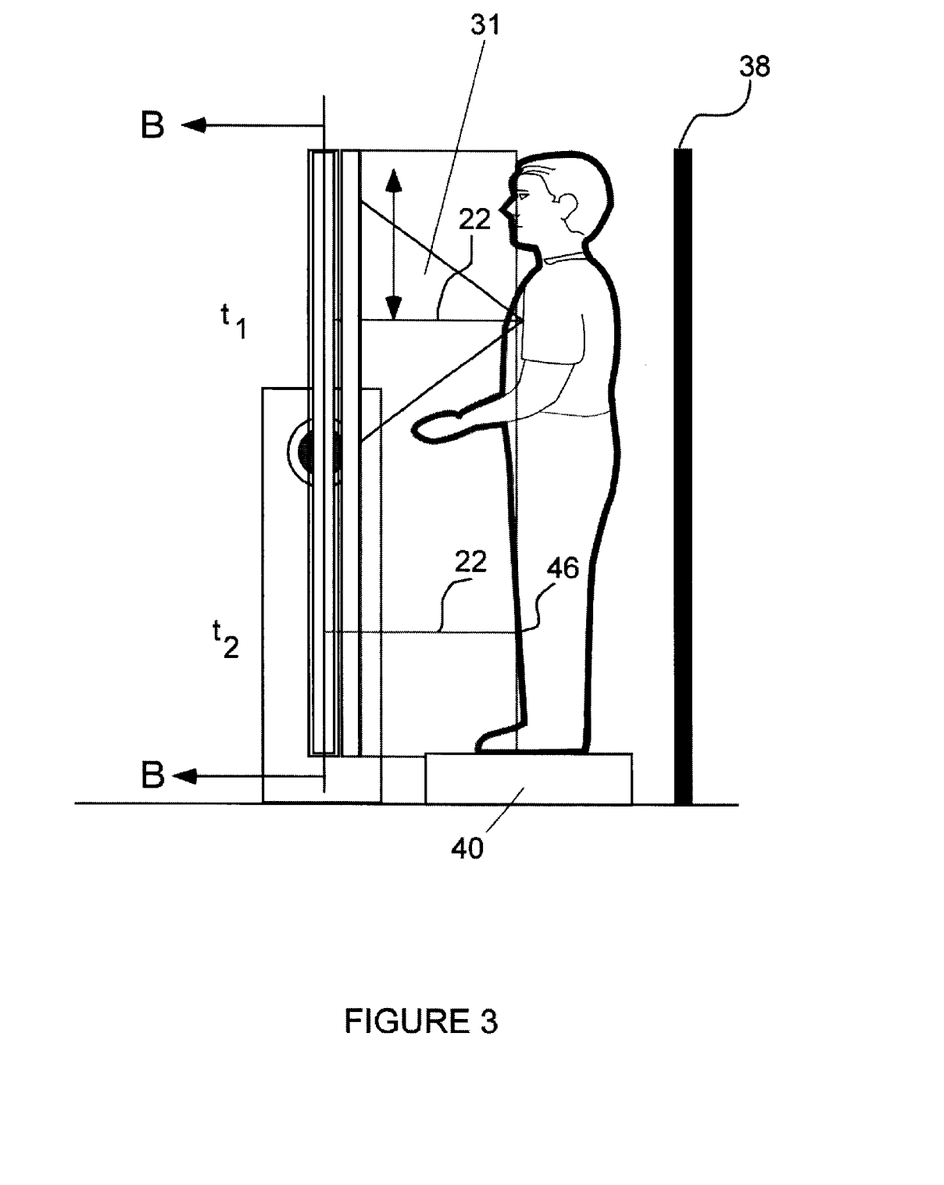
FIG. 3 is a side view of the personnel x-ray inspection system illustrated in FIG. 1.
Figure 4:
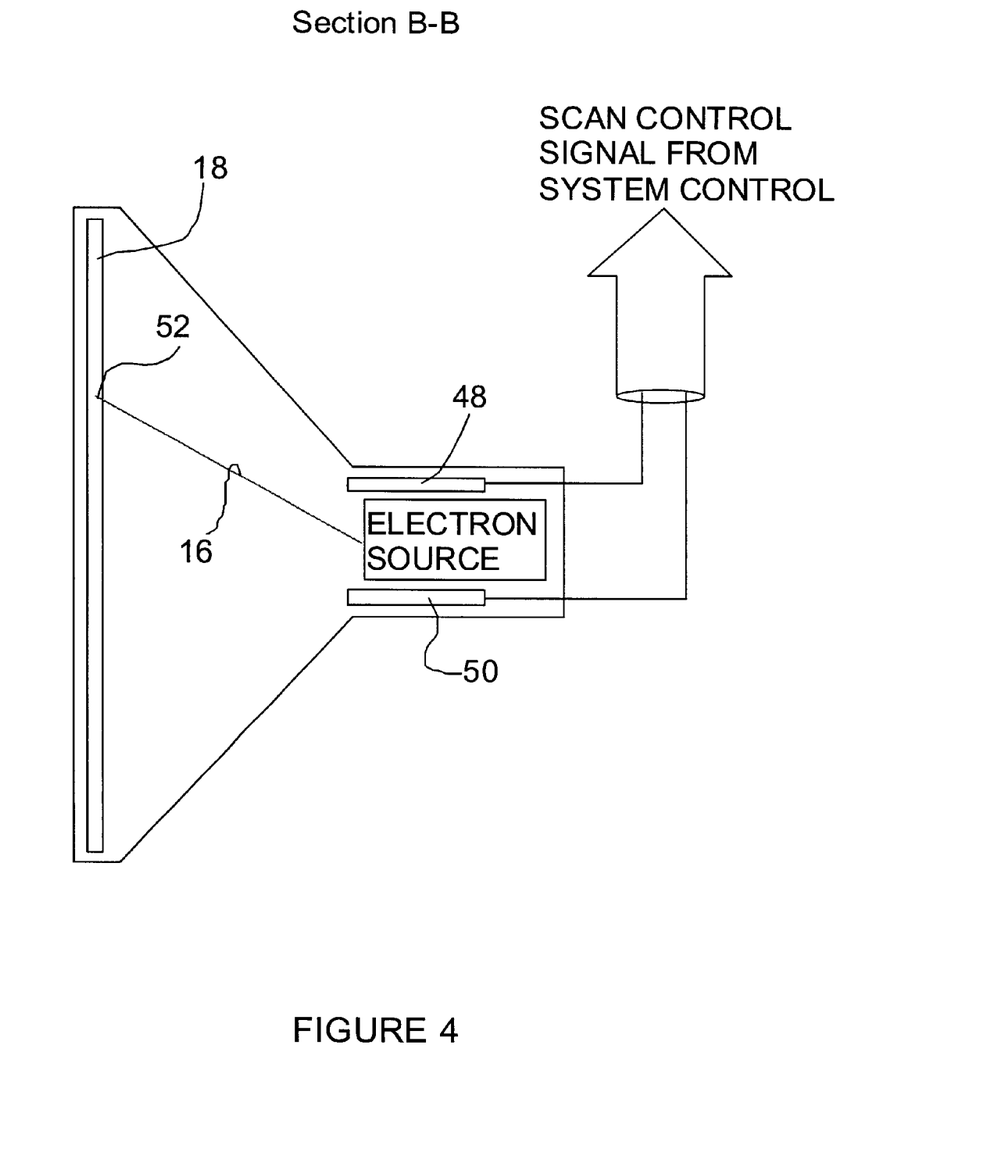
FIG. 4 is a sectional view taken along line B—B in FIG. 3 to illustrate the x-ray source.

FIG. 3 is a side view of the personnel inspection system 10. At time $t_1$, the collimated traveling pencil beam 28 strikes the person under inspection at a first position 44, and at time $t_2$ the collimated traveling pencil beam 28 strikes the person under inspection at a second position 46. In general, the electron beam is scanned along a vertical line on the anode 22. FIG. 4 is a simplified cross sectional illustration of the x-ray source 12 at time $t_1$ taken along line B—B in FIG. 3. As shown, electromagnets 48, 50 deflect the electron beam 16 such that it strikes the anode 22 (at time $t_1$ at location 52) to generate the cone of x-rays that is collimated to generate the pencil beam 28. Deflecting the electron beam in a controlled manner so it vertically scans along the vertically arranged target 22 and collimating the resultant cone of x-rays results in the collimated traveling pencil beam 28. Magnetic steering of an electron beam to generate a scanning x-ray beam to generate a scanning x-ray beam is known (e.g., U.S. Pat. No. 6,009,146 entitled "MEVSCAN Transmission X-ray and X-ray System Utilizing a Stationary Collimator Method and Apparatus" by Adler et al., which is incorporated herein by reference.)

Figure 5:
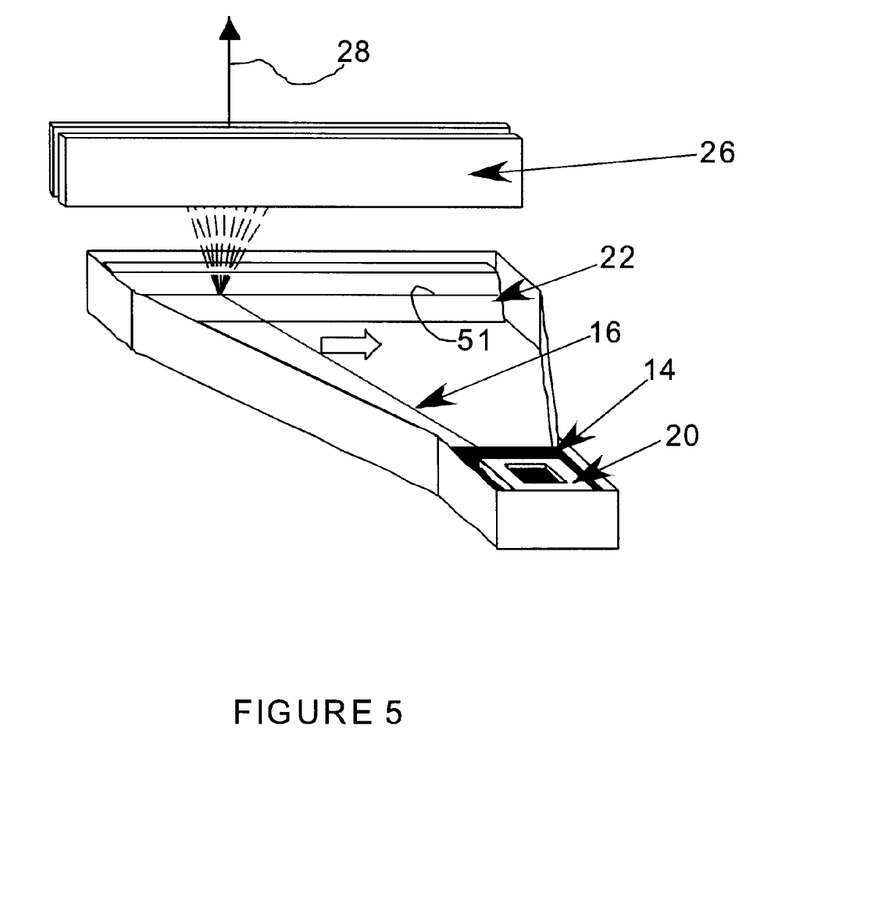
FIG. 5 is a perspective view of the x-ray source illustrated in FIG. 4.

FIG. 5 is a perspective view of the x-ray source illustrated in FIG. 4, which illustrates the target line 51 along which the deflected electron beam 16 is controllably scanned.

Referring FIGS. 1–5, advantageously the x-ray source 12 is much closer to the subject under inspection than in the prior art. This allows a smaller source strength because of the inverse square law. In addition, the fixed collimator 26 can be placed very close to the subject, which improves the spatial resolution of the image, allowing about a 1 mm resolution. In the prior art, the spatial resolution is of the order of a few mm or more because of the limited strength of the x-ray source. In addition, the maximum exposure to the subject, by FDA rule, is 10 micro-Roentgens, so that the image can only be improved by improving the spatial resolution at the maximum allowed x-ray exposure.

An additional advantage is that the x-ray anode 22 requires no cooling because the large area of the target and because the "dwell time" of the electron beam at each point on the target is only about 10 micro-seconds. Furthermore, the solid angle subtended by the backscatter detector 30 is much larger than in the prior art, because of the wrap around geometry, not possible in the prior art. This larger solid angle allows more data to be collected for a given x-ray exposure.

Because of the improved design the inspection time can be reduced to about 5 seconds/inspection.

While the subject is being rotated, other modes of inspection can be employed via other slits.

A problem with the rotating platform 40 is that the radiation exposure to different parts of the body will be different, depending upon the distance from the center of rotation to the surface of the body. In fact the radiation exposure is inversely proportional to this distance. Thus the exposure to the neck will be greater than the exposure to the midsection of the person, and a thin person will receive a larger dose than a fat person.

Figure 6:
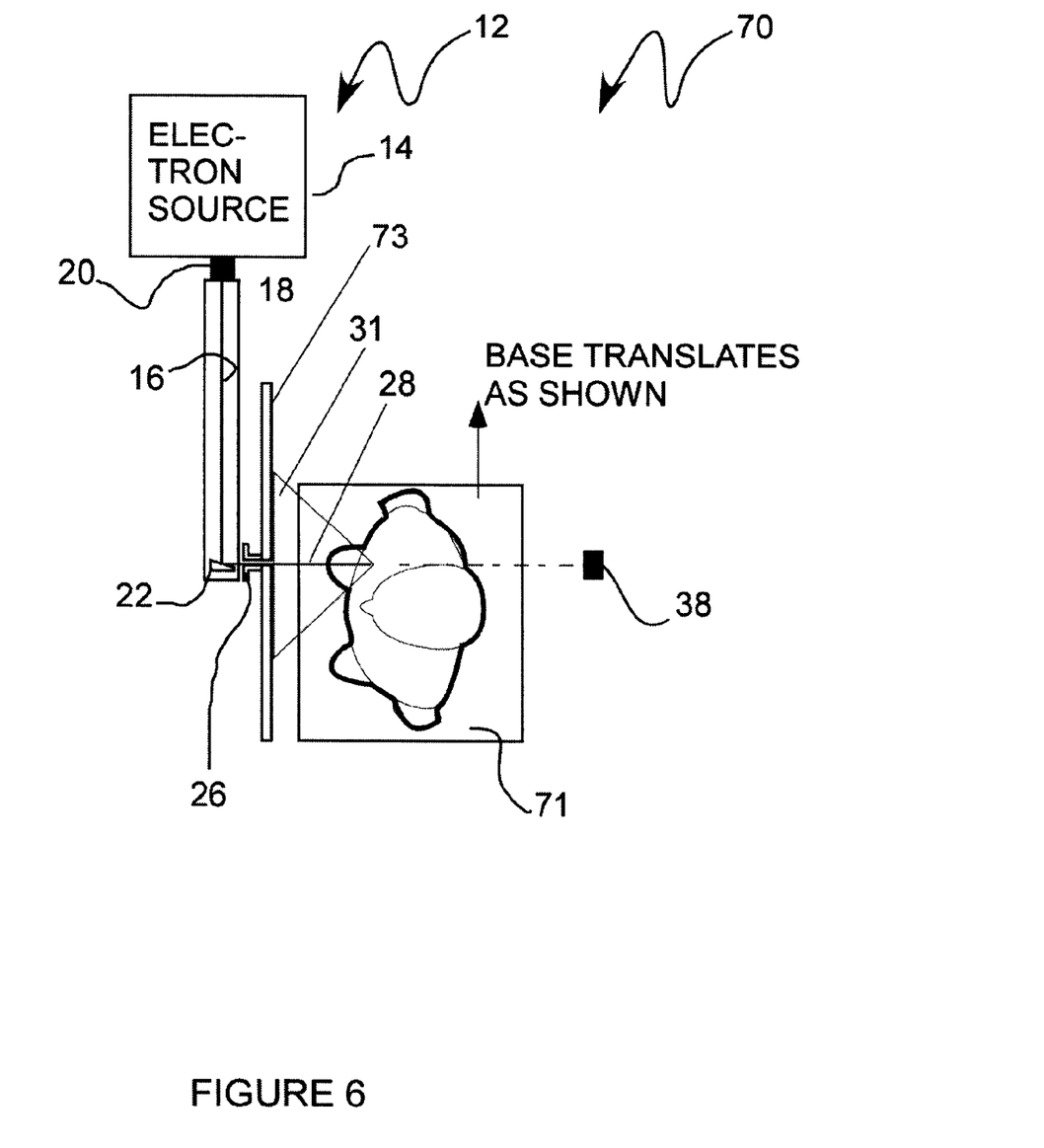
FIG. 6 illustrates a top view of an alternative embodiment personnel x-ray inspection system.
Figure 7:
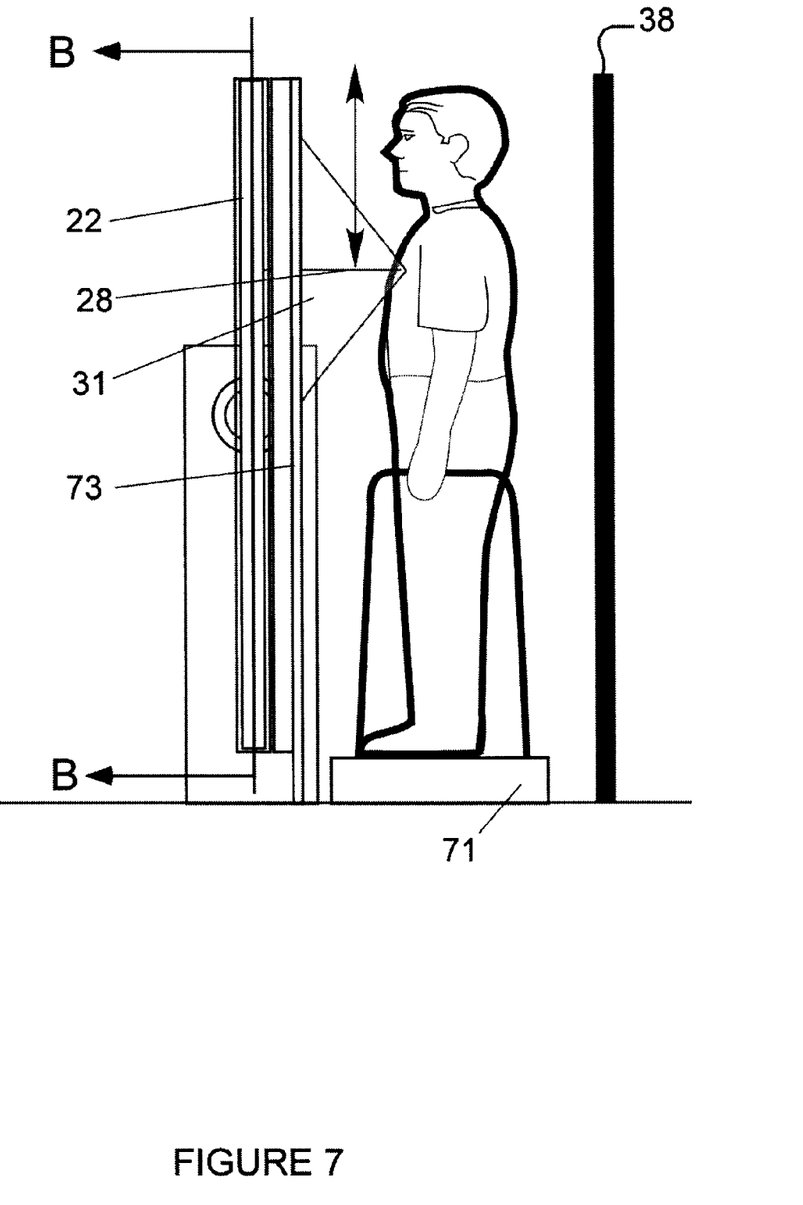
FIG. 7 illustrates a side view of the embodiment illustrated in FIG. 6.
Figure 8:
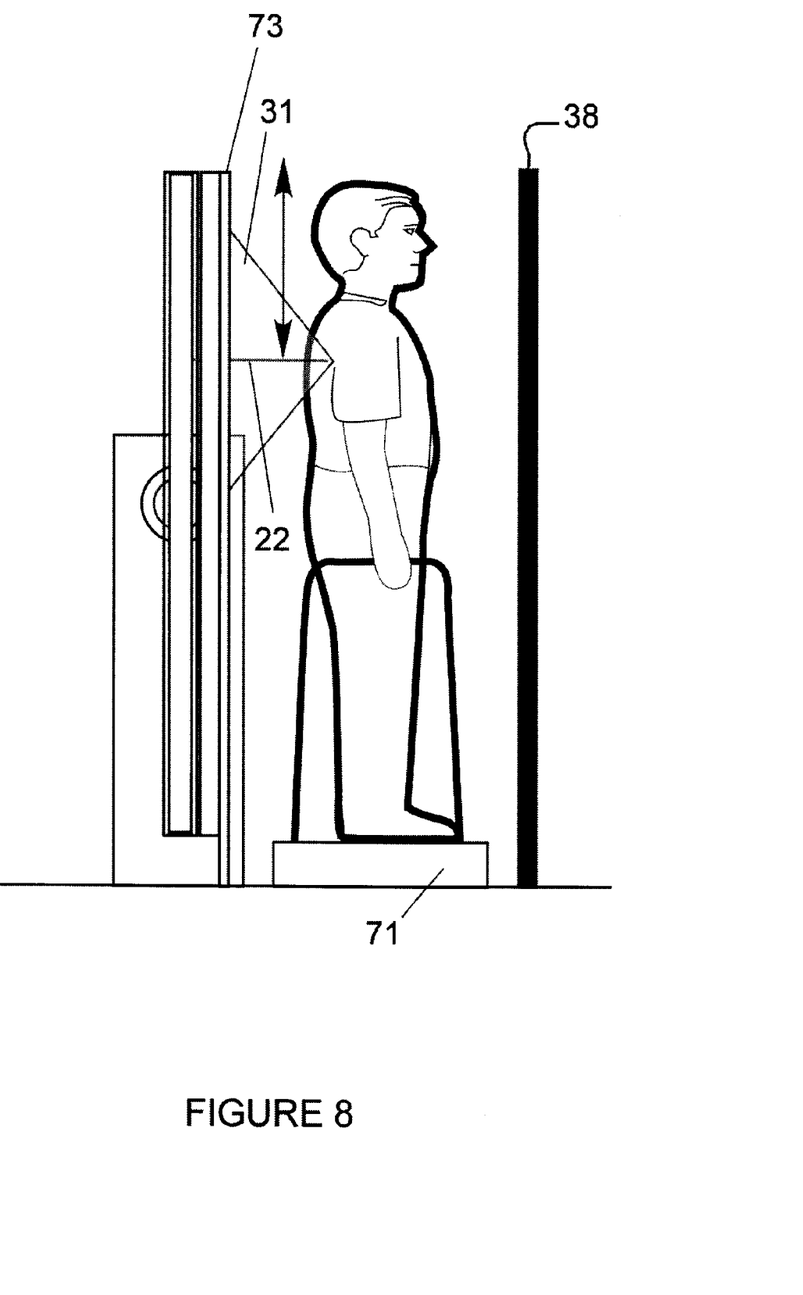
FIG. 8 illustrates the alternative embodiment personnel x-ray inspection system of FIG. 7, with the person under inspection turned around with respect to his position illustrated in FIG. 7.

FIG. 6 illustrates a top view of an alternate embodiment personnel x-ray inspection system 70. The system 70 is substantially the same as the system illustrated in FIGS. 1–5, with the principal exception that the alternative embodiment system 70 employs a moving (i.e., translating) platform 71 that carries the person under inspection across the line of x-rays 28. The movement of the platform 71 is into and out of the paper. The system 70 also includes a backscatter detector 73. In this alternative embodiment personnel x-ray inspection system 70 the backscatter detectors 73 are flat to allow passage of the person. The backscatter detectors 73 are preferably arranged on adjacent sides of the passage through which the x-ray pencil beams pass 28. FIG. 7 is a side view of the system illustrated in FIG. 6. As the person moves across the line of x-rays 28 as shown in FIGS. 6 and 7, an image of one side of the person is formed. The person then turns around as shown in FIG. 8, and the platform 71 reverses direction to image the other side of the person. Other views, such as a side image can also be taken.

The personnel inspection systems of the present invention can be used to uniquely identify a person. The identification techniques may include, for example, measuring a distance between anatomical markers such as width of head or distance between the eyes, and storing an x-ray image of the person in memory and use it as a template for future identification of the person. A person would find it almost impossible to change enough of his anatomy to defeat the system.

Figure 9:
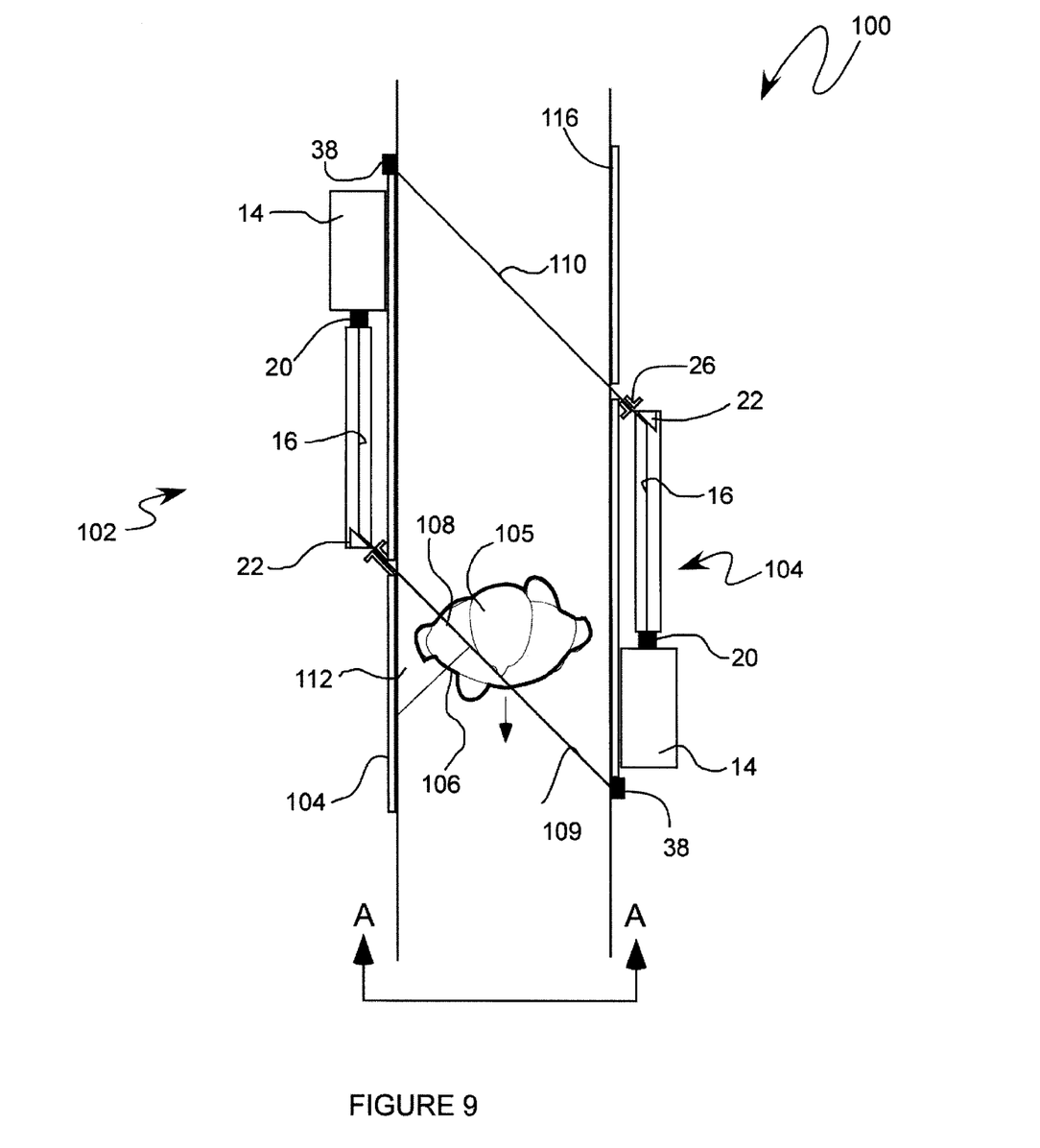
FIG. 9 is a top view of yet another alternative embodiment personnel x-ray inspection system.

FIG. 9 is a top view of yet another alternative embodiment personnel x-ray inspection 100. This system includes first x-ray imaging system 102 and a second x-ray imaging system 104. The first and second imaging systems 102, 104 are positioned on opposite sides of a pathway 105, and each of the first and second imaging systems is preferably substantially similar to the system illustrated in FIG. 6. However, in this embodiment, the person to be inspected can walk through the inspection system and be completely imaged, without having to be turned around and reinspected to image other side of the person under inspection.

Significantly, a first side 106 of the person to be inspected is imaged by a first scanning pencil beam 108, while a second side 109 of the person to be inspected is imaged by a second scanning pencil beam 110. Scattered x-rays 112 associated with the first scanning pencil beam 108 are detected by a first detector 114, and scattered x-rays associated with the second scanning pencil beam 110 are detected by a second detector 116. The detectors 114, 116 provide electrical signals to the system controller, which provides first and second images, respectively, for display to a system operator. That is, the first image is associated with the first side 106 of the person, while the second image is associated with the second side 109 of the person. The person can walk through and be x-rayed with or without his knowledge. In this embodiment, the translation of the body is accomplished as the person walks by the x-ray scanning pencil beam. Although the translation motion is not as uniform as in the case of a moving platform, a usable image for the purpose of detecting contraband is produced.

Figure 10:
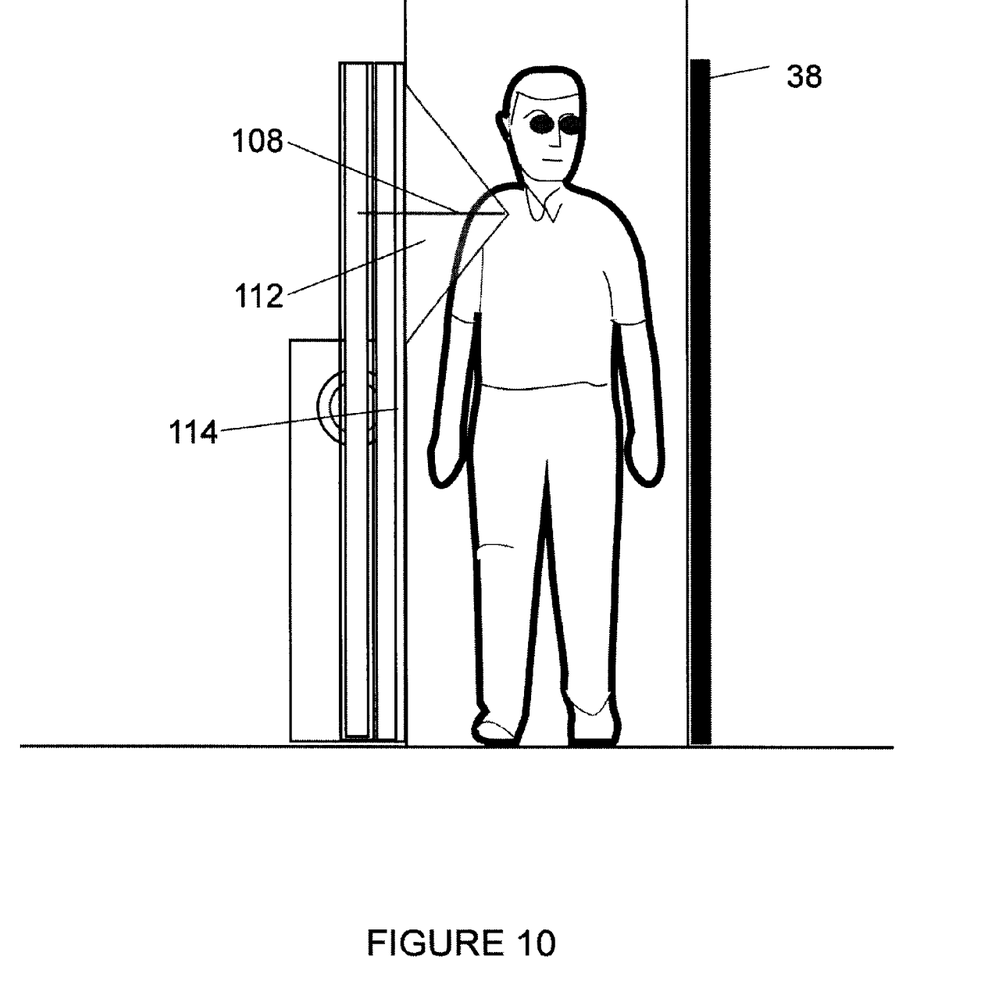
FIG. 10 is a side view of the alternative embodiment personnel x-ray inspection system illustrated in FIG. 9.

FIG. 10 is a side view of the alternative embodiment personnel x-ray inspection system illustrated in FIG. 9 taken along line A—A in FIG. 9.

Although the present invention has been shown and described with respect to several preferred embodiments thereof, various changes, omissions and additions to the form and detail thereof, may be made therein, without departing from the spirit and scope of the invention.

What is claimed is:

1. A personnel x-ray inspection system, comprising:
    an electron source that provides a pencil beam of electrons; an electromagnet assembly that receives said pencil beam of electrons and is configured and arranged to direct said beam of electrons along a line to form a scanning redirected beam under the control of a scan command signal;
    a target that is struck by said scanning redirected beam of electrons and generates a cone of x-rays that moves along a target line as a result of said scanning redirected beam;
    a collimator that receives said scanning cone of x-rays and generates a collimated traveling pencil beam, which is directed to a person under inspection;
    a rotating platform that translates the person under inspection through said collimated traveling pencil beam;
    a backscatter detector that detects backscattered x-rays, and provides a backscattered detected signal indicative thereof; and
    a system controller that provides said scan command signal, and which receives and processes said backscattered detected signal to provide an image signal indicative of the person under inspection.

2. The personnel x-ray inspection system of claim 1, comprising a narrow stationary beam catcher positioned to intercept x-rays that pass through the person under inspection.

3. The personnel x-ray inspection system of claim 1, wherein said backscatter detector is semi-circular shaped and includes a bisecting slit through which said collimated traveling pencil beam passes to the person under inspection.

4. A personnel x-ray inspection system, comprising:
    an electron source that provides a pencil beam of electrons;
    an electromagnet assembly that receives said pencil beam of electrons and in a controlled manner deflects said beam of electrons to form a scanning redirected beam of electrons under the control of a scan command signal;
    a target that is struck by said scanning redirected beam and generates a cone of x-rays that moves along a vertical target line as a result of said scanning redirected beam, wherein said target has a vertical length of at least about six feet;
    a stationary collimator that receives said scanning cone of x-rays and generates a collimated traveling pencil beam, which is selectively directed to a person under inspection through linearly offset holes in said stationary collimator;
    a rotating platform that rotates the person under relative to said collimated traveling pencil beam;
    a detector assembly that detects backscattered x-rays, and provides backscatter detected signal data indicative thereof;
    a system controller that provides said scan command signal to control the scanning of said beam of electrons to form a scanning redirected beam, and which receives and processes said backscattered detected signal data to provide an image signal indicative of the person under inspection; and
    a display device that receives said image signal and displays an image indicative thereof.

5. The personnel x-ray inspection system of claim 4, wherein said backscatter detector is semi-circular shaped and includes a bisecting vertical slit through which said collimated traveling pencil beam passes to the person under inspection.

6. The personnel x-ray inspection system of claim 5, comprising a beam catcher positioned to intercept x-rays that pass through the person under inspection.

7. The personnel x-ray inspection system of claim 5, wherein said pencil beam of electrons have a peak energy of about 70 to 200 KeV.

8. A x-ray inspection system, comprising:
    an electron source that provides a pencil beam of electrons;
    means for directing said beam of electrons along a line to form a scanning redirected beam under the control of a scan command signal;
    a target that is struck by said scanning redirected beam of electrons and generates a cone of x-rays that emanate from said target at locations along a straight target line running along said target as a result of said scanning redirected beam;
    a collimator that receives said scanning cone of x-rays and generates a collimated vertically traveling pencil beam, which is directed to a person under inspection;
    a rotating platform that translates an object under inspection through said collimated vertically traveling pencil beam;
    an x-ray detector assembly that detects backscattered x-rays, and provides a backscattered detected signal indicative thereof; and
    a system controller that provides said scan command signal, and which receives and processes said backscattered detected signal to provide an image signal indicative of the surface of the object under inspection.

9. The x-ray inspection system of claim 8, wherein said backscatter detector is semi-circular shaped and includes a bisecting slit through which said collimated vertical traveling pencil beam passes to the object under inspection.

10. The x-ray inspection system of claim 9, further comprising a display that receives and displays said image signal.

11. The x-ray inspection system of claim 10, wherein said means for directing comprises an electromagnet assembly.

12. A personnel x-ray inspection system, comprising:

a first electron source that provides a first pencil beam of electrons;

a first electromagnet assembly that receives said first pencil beam of electrons and is configured and arranged to direct said first beam of electrons along a line to form a first scanning redirected beam under the control of a first scan command signal;

a first target that is struck by said first scanning redirected beam of electrons and generates a first cone of x-rays that moves along a first target line as a result of said first scanning redirected beam;

a first collimator that receives said first scanning cone of x-rays, and generates a first collimated traveling pencil beam in a first direction that is directed to a passageway through which a person under inspection passes;

a first backscatter detector that detects first backscattered x-rays, and provides a first backscattered detected signal indicative thereof;

a system controller that provides said first scan command signal, and which receives and processes said first backscattered detected signal to provide a first image signal indicative of the person under inspection;

a second electron source that provides a second pencil beam of electrons;

a second electromagnet assembly that receives said second pencil beam of electrons and is configured and arranged to direct said second beam of electrons along a line to form a second scanning redirected beam under the control of a second scan command signal;

a second target that is struck by said second scanning redirected beam of electrons and generates a second cone of x-rays that moves along a second target line as a result of said second scanning redirected beam;

a second collimator that receives said second scanning cone of x-rays and generates a second collimated traveling pencil beam in a second direction parallel to said first direction, which is directed to said passageway through which the person under inspection passes, said second collimator being sufficiently far away from said first collimator so that a person can reasonably pass between the first and second collimators and be simultaneously imaged by x-rays generated by said first and said second targets;

a second backscatter detector that detects second backscattered x-rays, and provides a second backscattered detected signal indicative thereof; and wherein said system controller provides said second scan command signal, and receives and processes said second backscattered detected signal to provide a second image signal indicative of the person under inspection.

* * * * *